United States Patent [19]  [11] 4,035,339
Meyer-Stoll et al.  [45] July 12, 1977

[54] PROCESS FOR THE PRODUCTION OF FILM FORMING SYNTHETIC RESINS FOR HAIR FIXATIVES

[75] Inventors: Hans-Albrecht Meyer-Stoll, Rheinkamp-Repelen; Johannes Wöllner, Kapellen; Hans-Heinz Schittek, Moers-Meerbeck, all of Germany

[73] Assignee: Deutsche Texaco Aktiengesellschaft, Hamburg, Germany

[21] Appl. No.: 727,570

[22] Filed: Sept. 28, 1976

Related U.S. Application Data

[62] Division of Ser. No. 263,517, June 16, 1972, Pat. No. 3,987,010.

[30] Foreign Application Priority Data

May 29, 1968 Germany ............... 1770518

[51] Int. Cl.² ..................... C08G 12/06
[52] U.S. Cl. .............. 260/67.5; 260/33.4 R; 260/33.6 R; 260/72 R; 424/47; 424/71
[58] Field of Search ................ 260/67.5, 72 R

[56] References Cited

U.S. PATENT DOCUMENTS 3,649,597  3/1972  Henley .................. 260/67.5

FOREIGN PATENT DOCUMENTS 2,016,100  5/1970  France

OTHER PUBLICATIONS

Micchelli et al., Chemical Abstracts, vol. 70:31,625, (1969).

*Primary Examiner*—Howard E. Schain
*Assistant Examiner*—W. C. Danison, Jr.
*Attorney, Agent, or Firm*—Thomas H. Whaley; Carl G. Ries; James F. Young

[57] ABSTRACT

Process for the production of film forming synthetic resins for hair fixative compositions by reacting a methylolated 5,5-dialkylhydantoin containing 1–5 carbon atoms in each alkyl group at an elevated temperature in the presence of a bifunctional acid amide and/or amine. Hair fixative compositions containing 2–10% by weight of the resin product as the major or sole resin compound.

6 Claims, No Drawings

PROCESS FOR THE PRODUCTION OF FILM FORMING SYNTHETIC RESINS FOR HAIR FIXATIVES

This is a division of application Ser. No. 263,517 filed June 16, 1972, now U.S. Pat. No. 3,987,010.

The use of solutions of film forming synthetic resins in hair fixative compositions is known in the art. Liquid hair fixative compositions are used in the form of aqueous alcoholic solutions containing about 2-4% weight of lacquer raw materials or synthetic resins and minor amounts of perfume oil or similar agents. Hair fixative compositions suitable for application as aerosols, the so-called hair sprays, usually contain about 3-5% weight of film forming synthetic resin, anhydrous alcohols, such as isopropanol and/or ethanol, halogenated hydrocarbons, such as dichloromethane, which serves as a latent solvent and/or 25-75% weight of a propellant such as carbon dioxide or the fluorochlorinated hydrocarbons, e.g., the FREONS and auxiliary materials as perfume oils, plasticizers and the like.

Representative known film forming synthetic resins for hair fixative compositions are the polyvinylpyrrolidone (PVP) and PVP/vinyl acetate (VA) copolymers, modified acrylics, quaternized acrylics, methylvinylether-maleic anhydride copolymers, VA-crotonic acid copolymers, polyvinylimidazole, phthalic esters of pentaerythritol and 5,5-dimethylhydantoin-formaldehyde resins. Synthetic resins based on polyvinylimidazole and cellulose derivatives, although known to be used for hair fixative compositions, are generally less suitable for quality reasons. A disadvantage of synthetic resins based on polyvinylpyrolidone for hair fixative compositions is that they are hygroscopic and have an unpleasant odor. Moreover, these polymers and copolymers are relatively expensive. Also, it is known to be comparatively difficult to remove them from the hair by washing. Phthalic ester resins are disadvantageous because they tend to form scaly film on the hair which are hard to comb out.

Attempts have been made to eliminate the drawbacks of each of the above types of synthetic resins by mixing them with each other, which may result in a chemical interaction of the components, such as transesterification, etherification, and the like. For example, as shown in the German Published Pat. Application No. 1,254,292, minor amounts of a synthetic resin consisting of 5,5-dimethylhydantoin (DMH) and formaldehyde have already been used along with other materials in such mixtures. Synthetic resins of this type are known to be obtained by reacting DMH with an aqueous formaldehyde solution at elevated temperature in the presence of alkalis and optionally with an organic solvent. However, these known commercial DMH/formalin condensates used in hair fixative compositions have molecular weights lower than about 500 and tend to be sticky. Moreover, they are hygroscopic and tend to have a limited storage life. Accordingly, these low molecular weight condensates have only been used in conjunction with other resin condensates and then only in minor amounts.

It is known from U.S. Pat. No. 2,155,863 that water soluble resins can be prepared from 5,5 dialkyl hydantoins and formaldehyde and optionally also in the presence of the urea or phenol, which serve to harden the resulting resins. A known disadvantage of the resinous products prepared with urea is that as their melting point temperature range is increased above 100° C., the water solubility of the resulting resin products is materially reduced, that is, to a solubility substantially less than 50% even in hot water.

It is an object of the invention to produce a hair fixative composition whose synthetic resin component is an improved DMH/formalin condensate. Another object is to improve the known process for the production of DMH/formalin condensates in such a way that the products obtained have a relatively high molecular weight and are completely or largely free from the above disadvantages. A still further object is the formulation of a hair fixative composition containing an improved DMH/formalin condensate as the major resin component or as the sole resin component.

According to the invention these objects are achieved by a process for the production of film forming synthetic resin for hair fixative compositions by reacting at an elevated temperature a methylolated 5,5-dialkylhydantoin wherein each alkyl group contains from 1 to 5 carbon atoms, preferably 1 to 2 carbon atoms per alkyl group, in the presence of a lower aliphatic ketone and a bifunctional acid amide and/or an amine.

Further characteristics and advantages of the process according to the invention will become evident from the following description.

It has now been found that by carrying out the self-condensation reaction of a methylolated 5,5-dialkylhydantoin at an elevated temperature in the presence of a lower aliphatic ketone and a bifunctional acid amide and/or amine one is able to obtain a resin product of increased molecular weight in the order of from about 700 to 3000 or more which is free from the objectionable stickiness of the prior art condensates or in which this objectionable property is materially decreased and which has a solubility in water sufficient for the practice to permit it to be washed out of the hair in the usual manner.

Suitable temperatures for the condensation reaction mixture can vary from about 70° C. up to about 115° C. and higher dependent on the temperature of the reaction mixture at reflux.

In the condensation reaction one can use a lower alkanol or an aromatic hydrocarbon as a solvent or reaction diluent and as an aid in the removal of any water present. Representative solvents include methanol, ethanol, isopropanol, butanol and benzene.

In the process of the present invention it is desirable to carry out the methylolation of the 5,5-dialkylhydantoin with aqueous formaldehyde at an elevated temperature of from about 55° C. to about 100° C. and at a pH of from about 6 up to about 11. A particularly preferred procedure is to have the bifunctional acid amide present during the methylolation reaction. The formaldehyde and the bifunctional acid amide reactants are present in the methylolation reaction in the mole ratios of 1.5 to 2.5 moles, preferably 1.6 to 2.0 moles, of formaldehyde, and 0.2 to 2.5 moles, preferably 0.3 to 2.0 moles, of the bifunctional acid amide, per mole of the hydantoin.

It has been found that the molecular weights of methylolation products of DMH can be considerably increased and the stickiness of the products removed by effecting the methylolation in the presence of urea and a minor amount of a lower aliphatic ketone; molecular weight and "hardness" of the products increase with growing urea content. The ensuing deterioration of the water solubility of the prior art resin products is overcome without substantial change in the softening ranges of the synthetic resins by using the urea together with specified minor amounts of a lower ketone, such as acetone or methyl ethyl ketone. Furthermore, the urea may be wholly or partly replaced by a diamine, in particular ethylene diamine. The lower aliphatic ketone is used in an amount of from about 0.1 to 1.0 mole, preferably 0.2–0.3 mole per mole of urea. The amine is present in an amount of from 0.2 to 1 mole, preferably 0.3 to 0.5 mole, per mole of the hydantoin.

In the case of the amine additive it should preferably not be added until the methylolation of the DMH is completed and most or all of the water and/or any solvent are removed from the methylolated reaction products.

The use of the amine results in a further increase in the molecular weight of the products under the condensation reaction conditions. The preferred amines are ethylenediamine and propylenediamine. It has been found that this effect occurs also when using the higher molecular weight diamines, such as hexamethylenediamine, but the products produced with higher diamines are low-melting or somewhat sticky and therefore are less desirable.

By adding urea with the ketone and/or ethylenediamine, as reactants, according to the invention (urea having a quasi-hardening, the amine a quasi-plasticizing effect), it is now possible to effect the condensation reaction of the known methylolated reaction products of DMH with formaldehyde to form products having a solubility in water sufficient for the practice to permit them to be washed out of the hair in the usual manner and having a molecular weight of from about 700 to about 3000 or more, and which products can be made either "harder" or "softer" as required. The products of the invention are suitable to serve as the major or the sole film forming component in hair fixative compositions.

Following is a description by way of example of a method for carrying out the present invention.

COMPARATIVE EXAMPLE A 1.5 moles dimethylhydantoin (192 g) are charged together with 0.5 mole urea (30 g) and 2.0 mole formaldehyde (200 g of 30% formalin) to a reaction vessel typically used for condensation processes. The mixture is adjusted to the required $p_H$ value of 10 to 11 by adding 2N caustic soda solution. Thereafter the condensation reaction is conducted at 88° C. for 2 hours. The condensation is then continued under reduced pressure (15 mm $H_g$) and the reaction product concentrated by raising the temperature up to 135° C. After reaching this temperature the condensation is continued at 135° C. and under reduced pressure of 15 mm $H_g$ for two more hours. The solid resin obtained from the melt has a melting range of from 110° to 120° C. and only a poor water solubility. Even in hot water, far more than 50% of the resin remain undissolved. Consequently, this resin is unsuited for use in hair fixatives, as it cannot be completely removed by washing.

EXAMPLE 1

Comparative example A is repeated except that 0.1 mole acetone (5.8 g) is added. The resin thus obtained has a melting range of from 105° to 120° C. and is soluble in water as required. This resin is an excellent hair fixative ingredient, since it is not sticky owing to its high melting range and yet can be removed by washing.

EXAMPLE 2

115 grams (0.9 mole) 5,5-dimethylhydantoin, 18 grams (0.3 mole) urea, 3.5 grams (0.06 mole) acetone, and 150 grams (1.5 moles) 30% formalin, with the pH-value adjusted to 10–11 by means of NaOH, were reacted with agitation during 2 hours at 97°–98° C. The initial reaction product was then boiled down until solid, treated with 63 grams isopropanol and 1.2 grams concentrated hydrochloric acid, and further reacted with agitation for another 2 hours at 90° C. After neutralization with triethanolamine, the neutralized resin solution was concentrated under vacuum until the melting point of the resin product exceeded 90° C. The product obtained had a melting range of 96°–106° C.

EXAMPLE 3

384 grams (3 moles) 5,5-dimethylhydantoin, 60 grams (1 mole) urea, 500 grams (5 moles) 30% formalin, and 11.6 grams (0.2 mole) acetone were reacted with agitation at a pH-value of 10–11 and a temperature of 98° C. The solution was boiled down under vacuum until the residue had a melting point of 90°–95° C. The initial reaction product thus obtained was treated with 300 grams methanol and 5.5 grams concentrated hydrochloric acid and condensed for another 2 hours at 68°–72° C. After concentrating the solution under vacuum, a resin product having a melting range of 105°–115° C. was obtained.

EXAMPLE 4

The initial reaction product from Example 3 was treated with 350 grams n-butanol and 0.55 gram concentrated hydrochloric acid and further reacted for 3 hours at 113° C. After concentration under vacuum, a resin product having a melting range of 80°–90° C. was obtained.

EXAMPLE 5

256 grams (2 moles) 5,5-dimethylhydantoin, 60 grams (1 mole) urea, 58 grams (1 mole) acetone and 400 grams (4 moles) 30% formalin, with a pH-value of 10–11, were reacted with agitation for 2 hours at 85° C. and then concentrated under vacuum. A resin product having a melting range of 118°–130° C. was obtained.

EXAMPLE 6

256 grams (2 moles) 5,5-dimethylhydantoin, 60 grams (1 mole) urea, 11.6 grams (0.2 mole) acetone and 400 grams (4 moles) 30% formalin, with a pH-value of 10–11, were reacted with agitation for 3 hours at 96° C. and then concentrated to a highly viscous solution. The solution was treated with 200 grams methanol and 3.5 grams concentrated hydrochloric acid and further reacted for 3 hours at 73° C. After boiling down, a resin product having a melting range of 95°–115° C. was obtained.

EXAMPLE 7

80.6 grams (0.63 mole) 5,5-dimethylhydantoin were methylolated with 107 grams (1.07 moles) 30% formalin at 55° C. for 60 minutes, neutralized with triethanolamine and concentrated to a solids content of 95%. 100 grams isopropanol and 15.2 grams (about 0.2 mole) 80% ethylenediamine were added to the initial reaction product, and the resulting mixture was further reacted with agitation for another hour at 84° C., and then dehydrated using isopropanol azetrope. A light yellow resin solution was obtained which at 50% solids content had a viscosity of 1–2 minutes as measured in a 4 mm DIN cup at 20° C. The resin product began to melt at 106° C.

EXAMPLE 8

76.8 grams (0.6 mole) 5,5-dimethylhydantoin and 120 grams (1.2 moles) 30% formalin were reacted with agitation for 60 minutes at 88° C., neutralized with triethanolamine and concentrated to a solids content of about 95%. 200 ml. benzene and 23.8 grams (about 0.3 mole) 75% ethylenediamine were added and the resulting mixture was refluxed for 3 hours with removal of 22 ml. of water. After removal of the benzene by vacuum distillation a solid resin was obtained which started to get sticky at 100–110° C.

EXAMPLE 9

256 grams (2 moles) 5,5-dimethylhydantoin and 68.5 grams (0.5 mole) salicylamide were methylolated with 500 grams (5 moles) 30% formalin at a pH-value of 6 for 4 hours at 95° C., concentrated under vacuum and dyhdrated with benzene. The solution was adjusted to a pH value of 2 with hydrochloric acid and agitated for 5 hours at boiling temperature until dehydration was completed. After neutralization with triethanolamine and concentration, a faintly yellow resin product was obtained having a melting range of 76°–88° C.

The synthetic resins according to the invention from Examples 1–6 have osmometrically determined molecular weights of about 800–1200, and those from Examples 7 and 8 have molecular weights of 1500–3000.

EXAMPLE 10

The synthetic resin from Example 7 which when dry started to soften at 106° C., was used for preparing a solution containing 3.5% weight resin, about 66% weight anhydrous isopropanol and 30% weight dichloromethane. 60 grams of this solution and 40 grams of a mixture of FREON 11/12 (70:30) were filled into an aerosol spray can having a spin-effect nozzle. In the table below this solution is referred to as solution "A".

In a similar way another solution "B" was prepared using 1.8% weight each of the dry product from Examples 2 and 7.

Another solution "C" was prepared by mixing the product from Example 7 with a commercial vinylpyrrolidone/vinylacetatecopolymer (molar ratio 70:30) in a weight ratio of 4:1 using the same solvent as for "A" and "B", so that a total resin content of 3.5% weight resulted.

The properties of solutions A–C according to the invention, particularly their effectiveness as sprayable hair fixatives, were compared with those of commercial hair sprays. The solutions used for comparison contained the following film-forming agents:

Solution D: Phthalic ester
Solution E: Partially saponified polyvinyl acetate
Solution F: Vinylpyrrolidone/vinylacetate-copolymer (70:30)
Solution G: Dimethylhdantoin/$CH_2O$ condensate (molar ratio about 3:4; molecular weight about 480)

It should be noted that solution "G" was specially prepared for comparison purposes and did not constitute a commercial product. Although the condensate contained in solution "G" is commercially available for use in hair sprays, it is only employed in conjunction with other synthetic resins.

Each of the solutions A–G contained about 3.5% weight synthetic resin.

The properties of the hair fixatives A–G compiled in the table below were rated according to the following scheme:
1 = very good
2 = good
3 = satisfactory
4 = unsatisfactory

TABLE

| Solution | Hair Fixing Property | Facility of Combing | Scaling of Resin Film | Feel | Washability |
|---|---|---|---|---|---|
| A | 2 | 2 | none | 2 | 2–3 |
| B | 2 | 2 | none | 2–3 | 2 |
| C | 1–2 | 2 | none | 2 | 2 |
| D | 3–4 | 3 | none | 3 | 2–3 |
| E | 2 | 2 | none | 2 | 2 |
| F | 2–3 | 2 | none | 2–3 | 2 |
| G | 3–4 | 2–3 | heavy | 2 | 2 |

As shown in the table, compositions A–C containing the resin product of the invention are equivalent, if not superior, to the commercial hair spray compositions D–F. Moreover, the compositions A–C are practically colorless, odorless, not irritating to the skin and are neutral or at least non-corrosive. Where they show a weakly acid reaction, they can readily be neutralized; where they react alkalinely, neutralization with acids will result only in a slight discoloration without impairment of desirable properties. The compositions A–C can be readily mixed with each other without discoloration and therefore are suitable for mutual neutralization. The adjustment of a physiological pH-valve by mixing of the compositions is particularly advantageous. Furthermore, they are compatible with the addition thereto of minor amounts of conventional film forming resins, preferably such as vinylpyrrolidone/vinylacetate copolymers or oilfree phthalates.

We claim:
1. Process for the production of a water soluble, film-forming resin product having a molecular weight in the range of from about 700 up to about 3,000 or more, for a hair fixative composition which comprises reacting at an elevated temperature in the range of from about 70° C. to about 115° C. a methylolated 5,5-dialkylhydantoin wherein each alkyl group thereof contains from 1 to 5 carbon atoms, in the presence of from about 0.2 to about 1 mole of a diamine per mole of said hydantoin.

2. Process as claimed in claim 1 wherein said dialkylhydantoin is a methylolated 5,5-dimethylhydantoin.

3. Process as claimed in claim 1 wherein said diamine is ethylene diamine

4. Process as claimed in claim 1 wherein said diamine is present in an amount of from about 0.3 to about 0.5 mole per mole of said hydantoin.

5. Process as claimed in claim 1 wherein the reaction is carried out in a reaction diluent selected from the group consisting of a lower alkanol containing from 1 to 4 carbon atoms and benzene.

6. Process as claimed in claim 5 wherein said lower alkanol is at least one member selected from the group consisting of methanol, isopropanol and butanol.

* * * * *